United States Patent [19]

Kreuz

[11] Patent Number: 5,158,365
[45] Date of Patent: Oct. 27, 1992

[54] MEASURING PROBE

[75] Inventor: Hans-Otto Kreuz, Wilnsdorf, Fed. Rep. of Germany

[73] Assignee: Dango & Dienenthal Maschinenbau GmbH, Siegen, Fed. Rep. of Germany

[21] Appl. No.: 680,342

[22] Filed: Apr. 4, 1991

[30] Foreign Application Priority Data

May 28, 1990 [DE] Fed. Rep. of Germany ....... 4017176

[51] Int. Cl.⁵ .................. C21B 7/24; H01L 35/02; G01K 13/12
[52] U.S. Cl. .................. 374/138; 73/23.25; 73/863.41; 136/236.1; 374/179
[58] Field of Search ............... 374/179, 138, 139, 135; 136/234, 236.1; 252/962; 420/429; 73/23.25, 863.41

[56] References Cited

U.S. PATENT DOCUMENTS

| | | | |
|---|---|---|---|
| 2,285,457 | 6/1942 | Obermaier | 374/140 |
| 2,698,892 | 1/1955 | Hardin | 420/429 X |
| 3,508,910 | 4/1970 | Finlay et al. | 420/429 |
| 3,960,604 | 6/1976 | Heitzinger et al. | 374/139 X |
| 4,401,389 | 8/1983 | Theuwis | 374/140 |
| 4,548,517 | 10/1985 | Kampmann | 374/138 X |
| 4,721,534 | 1/1988 | Phillippi et al. | 374/179 X |
| 4,821,285 | 4/1989 | Johns | 374/139 X |
| 4,846,885 | 7/1989 | Asphahani et al. | 420/429 X |

FOREIGN PATENT DOCUMENTS 1408098 8/1970 Fed. Rep. of Germany .

OTHER PUBLICATIONS

"Binary Alloy Phase Diagrams", T. B. Massalski (Ed. in Chief) Cr-Mo (Chromium-Molybdenum), pp. 836-838 vol. 1.

Primary Examiner—Daniel M. Yasich
Attorney, Agent, or Firm—Anderson Kill Olick & Oshinsky

[57] ABSTRACT

A measuring probe for taking gas samples and/or making temperature measurements in furnace charges that are hot and/or have gas flowing through them, for example in blast furnaces, comprises a measuring head axially movable in a water-cooled sampling tube and having a thermocouple in a gas inlet opening, said head consisting at least in part of an alloy containing at least 90% molybdenum and characterized by a long service life.

9 Claims, 1 Drawing Sheet

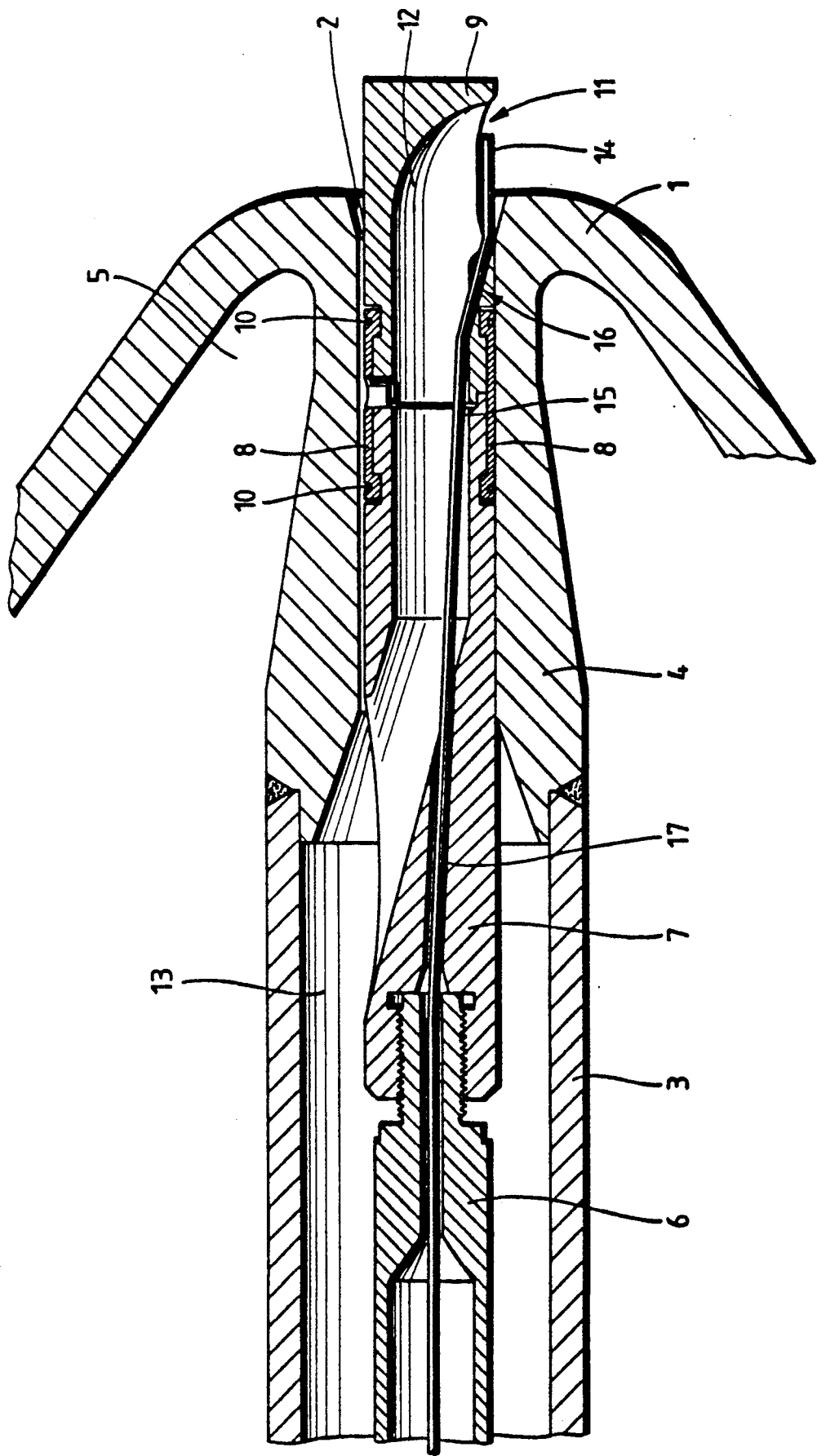

MEASURING PROBE

BACKGROUND OF THE INVENTION AND PRIOR ART

The invention relates to a measuring probe for taking gas samples and/or making temperature measurements in furnace charges that are hot and have gas flowing through them, comprising a measuring head that can be moved along in a sampling tube.

A measuring probe of this kind is known from German patent specification 1 408 098: it is useful for taking gas samples and temperature measurements in shaft furnaces, especially blast furnaces, and consists of a sampling tube which can be moved horizontally and has a sampling passage axially through it along which a hollow rod with a thermocouple can be moved. Spaced from the tip of the thermocouple the hollow rod has an annular collar having an external diameter substantially that of the, internal diameter of the sampling passage. By pushing the hollow rod along the tube, the tip of the thermocouple can be made to emerge into the ore burden filling the furnace shaft and the sampling passage simultaneously opened, so that gas can be sucked out at the same time as the temperature of the gas or of the interior of the furnace is measured.

Such measuring probes are subjected to severe mechanical stresses, since a force of as much as 70 tons is needed to introduce them horizontally into the coke, ore, pellets, sinter and scrap making up the furnace burden. The measuring head or the front end of the lance must withstand the corresponding surface pressure. and in addition is subjected to particularly high stress when it is moved out of the probe or its sampling tube to make a measurement, as it is then surrounded on all sides by the furnace burden and by the hot flowing furnace gases. The probe and the measuring head are subjected to high bending forces and severe wear and tear both by the descending furnace burden and by the dust contained in the gas, which acts as a sand blast because of its high velocity. In addition there is the danger of caking on, especially of alkalis, and the danger of hot corrosion by the reducing furnace gas, containing inter alia alkalis, hydrogen, hydrocarbons, sulphur dioxide and metal oxides.

Although the known measuring probe has proved satisfactory, especially in blast furnaces, it has reached the limit of its utility in present-day blast furnace operation on account of increasing furnace temperatures due to the blowing in of oil and coal dust and the resulting extremely high stresses, since the measuring head needs to have high strength and resistance in all respects, as otherwise it cannot be pushed along in the sampling passage. In particular it must not be subject to distortion or scaling and formation of deposits, as otherwise the measuring head will jam in the sampling passage and block the gas passage.

Attempts to improve the cooling of the sampling tube and/or the measuring head to make introduction at higher operating temperatures possible have been unsuccessful, since the associated greater removal of heat cannot but influence the surroundings of the measuring head and/or the results of the measurements.

As a result of this the temperature at which conventional measuring probes can be used is limited to about 1100° C. In addition the more frequent replacement of the measuring head, made necessary by increasingly high temperatures, requires the measuring probe to be withdrawn each time from the pressurised furnace and the new one to be introduced into the furnace or the furnace charge. Because of the high temperature and the pressure in the furnace, this requires considerable effort and exposure to danger on the part of the operating team.

OBJECT OF THE INVENTION

It is therefore an object of the invention to provide a measuring probe having a measuring head that is not directly cooled but which is both characterised by a long service life and can withstand use at high to very high temperatures, for example temperatures of up to 1350° C.

SUMMARY OF THE INVENTION

The solution of this problem has been found to lie in the use of an alloy containing at least 90% molybdenum for at least part of the measuring head, despite the fact that even at a low red heat molybdenum undergoes marked oxidation, which would in itself prevent the high hot strength and thermal conductivity of molybdenum and its molybdenum-rich alloys from being used under conditions such as those prevailing in the shaft of a blast furnace.

Surprisingly it has however been found that a measuring head consisting of an alloy of at least 90%, for example 95% or even 99% molybdenum, can well withstand the particular stresses in the blast furnace shaft. There the measuring head is not only exposed to temperatures above 1000° C., but also to the descending furnace burden and to furnace gas of different compositions. Not only does the gas composition vary from furnace to furnace, but for example also across the cross-section of a blast furnace, for example within the range 1.3 to 1.5% hydrogen, 17 to 30% carbon monoxide, 11 to 26% carbon dioxide and 54 to 56% nitrogen. Added to this are the vapours of a wide variety of oxides and alkalis. Equally varied, but in every case extremely severe, are the stresses on the measuring head, which must also withstand the mechanical stresses of the constituents of the furnace burden, which are still relatively hard at temperatures above 1000° C. Moreover there is a danger of carburization, since the carbon dioxide in the off-gas breaks down to form carbon which goes into solution and forms carbide and can lead to hardness cracking. Clearly, however, under the operating conditions a carburised, i.e. substantially carbidic, surface zone with improved wear resistance must be formed, which leads to a substantial increase in the time to failure.

The measuring head alloy with at least 90% molybdenum according to the invention can be produced by powder metallurgy and can also — particularly in order to improve its mechanical and thermal properties — contain up to 10% in all of one or more of iron, manganese, nickel and silicon, together with impurities arising from melting, as the balance. Preferably however the molybdenum content is at least 99%, in order to obtain the greatest resistance to corrosion, particularly to sulphidation and siliconising, thermal conductivity and thermal shock resistance. For the most severe conditions the measuring head alloy should contain 99.9% molybdenum and some 100 ppm of zirconium finely distributed therein. At lower molybdenum contents the zirconium content is preferably at least 2000 ppm.

To reduce the consumption of high-grade materials without greatly impairing its life, the measuring head can be joined to a measuring head carrier, preferably by clamping. This carrier is preferably combined with a push-tube which serves to move the measuring head out of the sampling tube and may consist of an inexpensive steel.

For taking gas samples the measuring head may be provided with a central gas withdrawal passage, the mouth of which preferably opens in the side of the measuring head and thus can be on the side sheltered from the descending furnace burden but simultaneously open in the direction of flow of the furnace gas. The thermocouple for the temperature measurement should project into the mouth of the passage and is preferably mounted in the wall of the measuring head.

BRIEF DESCRIPTION OF THE DRAWINGS

The invention will now be described in more detail, by way of example, with reference to an embodiment illustrated in the accompanying drawing, which shows the front part of a cooled measuring probe.

DETAILED DESCRIPTION OF A PREFERRED EMBODIMENT OF THE INVENTION

The measuring probe consists of a sampling tube 1 with a funnel-shaped mouth 2, a concentric sampling passage 3,4 and an annular passage 5 through which coolant flows. A movable push-tube 6 passes axially through the sampling passage 4 and is screwed to a measuring head holder 7. The measuring head holder is in turn clamped to the cylindrical measuring head 9, which is substantially L-shaped in section, by means of two half-shells 8. For this purpose circlips 10 are provided at the front ends of the two half-shells 8. A gas sampling passage 12 extends from the downwardly-pointing mouth 11 of the measuring head 9 through the measuring head and the holder 7 attached thereto and leads eccentrically into an annular space 13 that surrounds the push-tube 6 and is connected with a gas analysis apparatus, not shown.

In the mouth 11 of the passage 12 there is a thermocouple 14, whose leads 15 run through a bore 16 in the measuring head 9 and through the gas sampling passage 12 and a bore 17 in the measuring head holder 7 and then through the push-tube 6 to an indicator device, not shown.

The measuring head 9 consists of an alloy as set forth in claim 1, containing at least 90% molybdenum and having high hardness and tensile and creep strength, high yield strength and low coefficient of thermal expansion, together with appropriate toughness. It need be no longer than is required by the temperature of the furnace gas entering the passage 12, which decreases in the direction of flow. The extent of reduction in temperature in the gas removal passage 12 is unimportant, since all that matters is that the gas temperature at the mouth 11 of the passage and in the neighbourhood of the thermocouple 14 is not affected and substantially corresponds to the gas temperature in the furnace.

What is claimed is:

1. A measuring probe for use in taking gas samples and making temperature measurements in furnace charges, comprising a measuring head that can be moved along in a sampling tube for gas sampling purposes wherein the measuring head is at least in part made of an alloy consisting essentially by weight of at least 90% molybdenum and up to 10% of at least one of chromium, iron, nickel, manganese and silicon, together with impurities resulting from melting, the measuring head being clamped to a measuring head holder.

2. A measuring probe according to claim 1 wherein the alloy consists of at least 99% molybdenum.

3. A measuring probe according to claim 1, wherein the alloy also contains zirconium.

4. A measuring probe according to claim 3, wherein the zirconium content is at least 2000 ppm (parts per million).

5. A measuring probe according to claim 1, wherein the measuring head is connected to a push-tube.

6. A measuring probe according to claim 1, wherein the measuring head is provided with a centrally arranged gas-removal passage.

7. A measuring probe according to claim 6, wherein the gas-removal passage opens in a side of the measuring head.

8. A measuring probe according to claim 7, wherein the thermocouple has leads that pass through a wall of the measuring head.

9. A measuring probe according to claim 6, wherein a thermocouple projects into a mouth of the gas-removal passage.

* * * * *